(12) United States Patent
Hoernig

(10) Patent No.: US 7,560,682 B2
(45) Date of Patent: Jul. 14, 2009

(54) DEVICE AND METHOD FOR MONITORING SOLID-STATE DETECTORS

(75) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/052,860

(22) Filed: Mar. 21, 2008

(65) Prior Publication Data

US 2008/0232555 A1  Sep. 25, 2008

(30) Foreign Application Priority Data

Mar. 21, 2007 (DE) .................. 10 2007 013 620

(51) Int. Cl.
*G01D 18/00* (2006.01)
*G01T 1/24* (2006.01)

(52) U.S. Cl. .............. 250/208.1; 250/370.09; 378/98.8; 378/207

(58) Field of Classification Search .......... 250/208.1, 250/370.01, 370.08, 370.09; 378/98.8, 207
See application file for complete search history.

(56) References Cited

U.S. PATENT DOCUMENTS

| 5,047,863 | A | * | 9/1991 | Pape et al. ............. 348/247 |
| 5,272,536 | A | * | 12/1993 | Sudo et al. ............ 348/243 |
| 5,657,400 | A | | 8/1997 | Granfors et al. |
| 5,854,655 | A | * | 12/1998 | Watanabe et al. ........ 348/247 |
| 6,529,618 | B1 | * | 3/2003 | Ohara et al. ............ 382/132 |
| 6,529,622 | B1 | * | 3/2003 | Pourjavid ............. 382/149 |
| 6,623,161 | B2 | * | 9/2003 | Aufrichtig et al. ....... 378/207 |
| 6,663,281 | B2 | * | 12/2003 | Aufrichtig et al. ....... 378/207 |
| 6,919,568 | B2 | * | 7/2005 | Odogba et al. ....... 250/370.09 |
| 7,078,693 | B2 | * | 7/2006 | Nonaka .............. 250/336.1 |
| 7,085,408 | B1 | * | 8/2006 | Chung-Chi Jim ........ 382/149 |
| 7,116,811 | B2 | * | 10/2006 | Leveau-Mollier ........ 382/132 |
| 2002/0149684 | A1 | * | 10/2002 | Leveau-Mollier ........ 348/246 |
| 2007/0057170 | A1 | | 3/2007 | Hornig |

OTHER PUBLICATIONS

"Correction of Amplifier Non-Linearity, Offset, gain, Temporal Artifacts, and Defects for Flat Panel Digital Imaging Devices," Wischmann et al., Proceeding of SPIE, vol. 4682 (2002) pp. 427-437.
"Electronic Transport Properties of Stabilized Amorphous Selenium X-ray Photoconductors," Fogal, University of Saskatchewan Master Thesis (2005).

* cited by examiner

*Primary Examiner*—John R Lee
(74) *Attorney, Agent, or Firm*—Schiff Hardin LLP

(57) ABSTRACT

In a device and associated method for monitoring solid-state detectors, image segments of a test image (such as, for example, a dark current image) from solid-state detectors are evaluated and further usability of the solid-state detector is indicated using assessment criteria.

12 Claims, 3 Drawing Sheets

DEVICE AND METHOD FOR MONITORING SOLID-STATE DETECTORS

BACKGROUND OF THE INVENTION

1. Field of the Invention

The present invention concerns a device and a method for monitoring of solid-state detectors formed with amorphous semiconductor materials.

2. Description of the Prior Art

Solid-state detectors (which are subsequently also designated as flat panel detectors or image detectors) can be fashioned as flat x-ray detectors. The solid-state detectors are used in, among other things, mammography or radiology. Digital x-ray images can be measured at the solid-state detectors after the incidence of high-energy radiation thereon. In the solid-state detectors considered herein the principle of direct conversion can be used for x-ray image generation. In this principle charges are generated by high-energy radiation striking the amorphous semiconductor material. The charges generated in the amorphous semiconductor material are then discharged by means of a readout electronic formed with a thin film transistor (TFT) semiconductor technique and evaluated in downstream electronic processing units. The employed amorphous semiconductor material (which can be, for example, amorphous selenium a-Se) can tend toward crystallization upon exceeding or dropping below an operating or environment temperature. Upon such crystallization, the state of the amorphous selenium irreversibly changes to a crystalline state. This has the consequence that the image quality of the flat panel detector or image detector is reduced.

SUMMARY OF THE INVENTION

An object of the present invention is to provide a method and a device for monitoring the semiconductor material of a solid-state image detector with regard to properties of the semiconductor material that may degrade the image produced by the image detector.

It is a further object to provide such a method and a device that allow monitoring of the crystallization of amorphous semiconductor material in such a solid-state detector.

The above object is achieved in accordance with the present invention by a method and a device wherein an image acquisition unit for storage of a test image is provided in a monitoring unit, and wherein signal values respectively from different regions of the test image are compared with predetermined thresholds and, from these original comparisons, the suitability of the image detector for further use is determined and indicated.

The invention has the advantage that crystallization in the detector elements is detected.

The appertaining crystallization regions on the flat panel detector can be marked by graphical elements.

The inventive monitoring can ensue continuously.

The quality of the flat panel detector can be objectively assessed and a prediction about its usable duration is possible.

An image degradation caused by crystallization can be used as a possible basis for an error correction.

DESCRIPTION OF THE PREFERRED EMBODIMENTS

Figure 1:
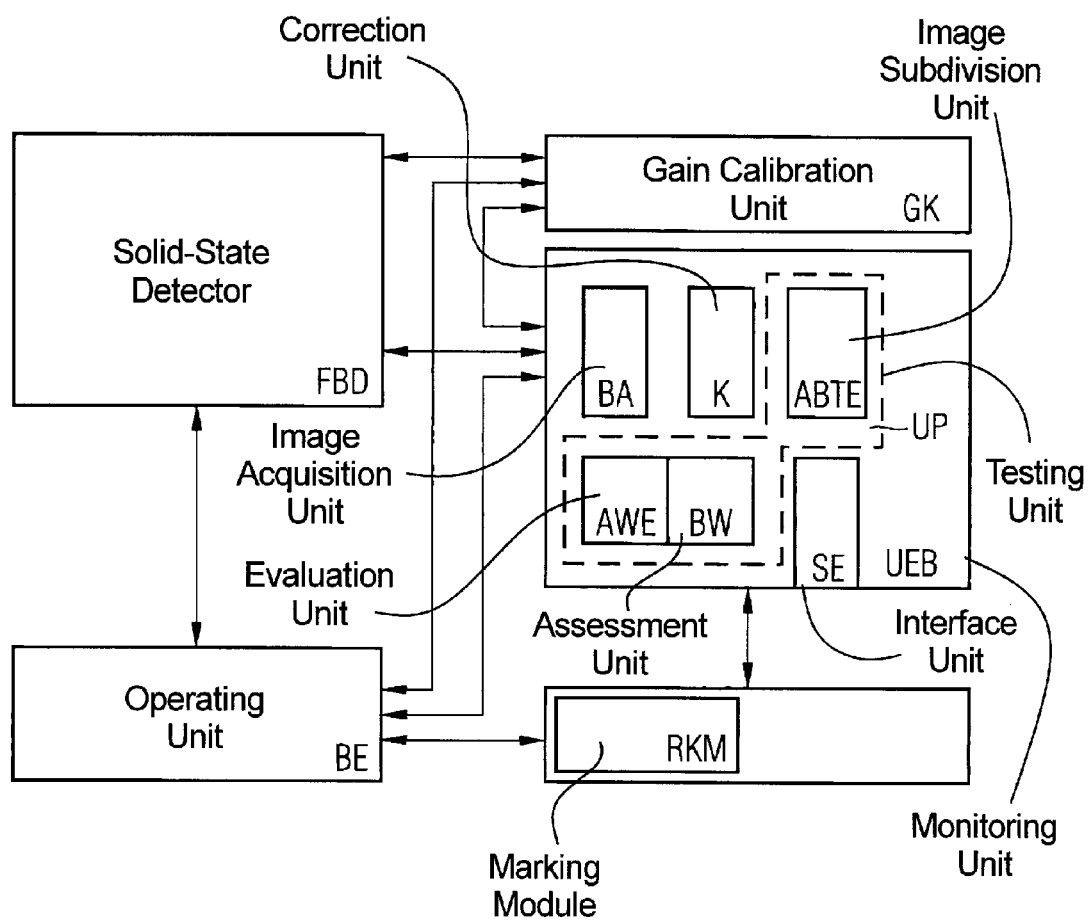
FIG. 1 is a block diagram of a device for monitoring a semiconductor detector in accordance with the invention.

A block diagram for detector monitoring is shown in FIG. 1. The components shown in this block diagram are an operating unit BE, a flat panel detector FBD, a monitoring unit UEB and optionally a gain calibration unit GK and a marking module RKM for localized crystallization areas.

The monitoring unit UEB includes, among other things, an image acquisition unit BA, a correction unit K, a testing unit UP as well as an interface unit SE. Among other things, an image subdivision unit ABTE, an evaluation unit AWE and an assessment unit BW are comprised in the testing unit UP.

Prompted by a control signal generated in the monitoring unit UEB, a backlight exposure or a dark image (which is also designated as a rest image or dark current image) is retrieved from the flat panel detector FBD, for example. As an alternative to such image acquisition without the use of the x-ray source, cached images from a gain calibration unit GK can be retrieved. The imported test images such as dark current images or gain-calibrated images are cached in the image acquisition unit BA. The cached images can be offset-corrected, defect-corrected and gain-corrected in the correction unit K depending on the image source. The test image is sampled in the manner described in the following after atypical deviations in the signal grey level that can suggest a beginning or existing crystallization process. For example, the analysis begins with the consideration of image segments SEG1, SEG2 at the detector image border since the process of the crystallization first occurs in the border regions. In the evaluation unit AWE signal grey values of image segments with N pixel segments Px at, for example, 64×64 pixels or image points are extracted from the cached image for a subsequent assessment of the flat panel detector. As an alternative to this, signal grey values of pixel segments with 256×256 pixels can also be determined. The variance, the average, min-value and max-value of the grey values of the pixel segments are determined for each of the image segments SEG1, SEG2, SEGZ (N=12) formed from, for example, N=6 pixel segments Px. A comparison with a normal, typical grey value is required in order to declare a pixel grey value or pixel segment grey value as atypical. This can be determined by averaging or/and standard deviation as well as variance via storage of an image or the subsequent analysis of a pixel region upon the delivery or installation of the flat detector. The normal, typical grey value from a region of the current image can likewise be learned. This central region could be the central region of the flat panel detector FBD since it is typically not affected or is affected only very late by a crystallization. An image segment SEGZ with, for example, 12 pixel elements Px is selected in the center of the flat panel detector FBD and the average, the variance, min, max etc. are calculated to determine the reference grey value. The averages, variances, standard deviations, min, max are calculated in the evaluation unit AWE and inserted into a first through, for example, fourth assessment rule R1, R2, R3 or R4, whereby by drawing upon the first through, for example, fourth thresholds SWWA, SWWB, SWWC and SWWD associated with the assessment rules it is respectively decided whether an assessment criterion is satisfied. The mean square deviation of the discrete signal from the average is described with the variance.

$$\text{var}=\sigma^2=1/N*\text{sum}(N)(S(x,y)-\text{mean})^2$$

$$R1 = [\text{mean}(SEGZ) - \text{max}(SEG2)] > SWWA$$

$$R2 = \text{max}(SEG2) > SWWB \times \text{max}(C)$$

$$R3 = [\text{var}(SEG1) - \text{var}(SEG2)] > SWWC$$

$$R4 = \text{number of image segments with var}(SEG2)$$
$$> SWWD \geq 2$$

For example, a first assessment criterion R1 is present when the difference of the calculated average of the signal grey values in the reference segment SEGZ minus the maximum value of the signal grey value from the second border region segment SEG2 is greater than the first threshold SWWA.

The assessment of the image detector analysis ensues, for example, in a cascaded manner, meaning that a plurality of criteria such as R1 and R2 must be satisfied. A classification can be effected using the satisfied criteria. For example, if R1 and R2 are satisfied, a beginning local crystallization exists and corresponding signals S1, S2, S3, . . . ensue to a service unit C, BE. If the criteria R1 through R4 are satisfied, the detector is to be replaced.

The assessment criteria R1 through Rn or, respectively, thresholds SWWA, . . . , SWWD are derived and established based on artifacts (such as, for example, crystallization) and from a statistical analysis of a long-term observation of detectors. By drawing on a probability of crystalline regions to be expected on the flat panel detector FBD, values of standard deviations of grey values of image segments from the border regions are compared with at least one standard deviation value of a reference segment SEGZ from the region of the image center of the flat detector FBD. If the values deviate more significantly from one another than a predeterminable specific acceptance limit, at least one local crystallization exists here, based on the assessment criteria R1, R2, R3 and R4. In an alternative embodiment a plurality of region segments must exhibit a crystallization, or region segments that do not lie directly at the image edge must be affected. It is also conceivable that at least two assessment criteria are drawn upon to identify an artifact.

Figure 2:
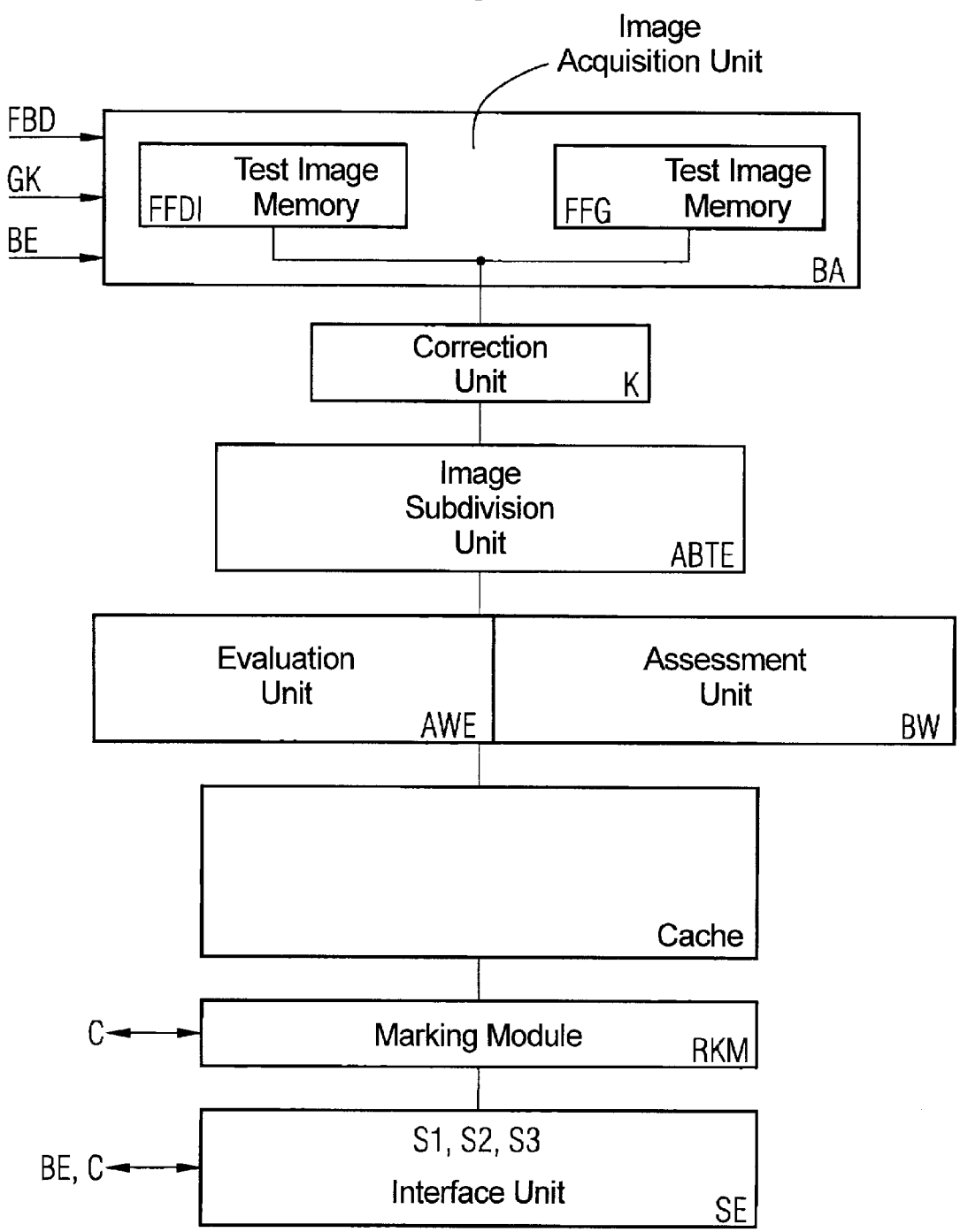
FIG. 2 is a flowchart of an embodiment of the inventive method.

A flowchart for determination of possible crystalline regions on the flat panel detector/solid-state detector FBD is reproduced in FIG. 2. According to this flowchart diagram the test image to be assessed arrives either from the solid-state detector FBD or from a gain calibration unit GK directly into a first cache unit Flat Field Dark Image FFDI or second cache unit Flat Field Image Gain-calibrated FFG of the image acquisition unit BA. The functions of the correction unit K, of the image sub-division unit ABTE and of the image evaluation unit AWE are described above. A crystallization region is determined in the assessment unit BW corresponding to the following rules. Starting from the calculation of the variance or the average values, min, max regarding the image segments SEG1, SEG2 and SEGZ and predeterminable thresholds SWWA, SWWB, SWWC, SWWD, a decision is made about a further use of the assessment criteria R1, R2, R3 and R4. A crystallization then exists when, for example, two of the criteria R1, R2, R3, R4 are satisfied. Signaling can subsequently ensue in different ways. The values of the assessment criteria are sent to a service center or a control unit C via, for example, remote service, e-mail etc. An exchange of the flat panel detector FBD could be prompted by a first signaling S1 in connection with the assessment criteria. The appertaining detector region can be indicated to the operator or service technician via a service interface with a second signaling S2. This region can then be observed in detail or, respectively, zoomed out. A possible further usage duration of the flat panel detector can be visibly displayed with a third signaling S3. The further use of the flat panel detector can thereby extend from an immediate deactivation to a limited operation with the request to exchange the detector plate. The first, second or third signaling S1, S2, S3 can also ensue to a control unit C or an operating unit BE of the diagnosis system.

Figure 3:
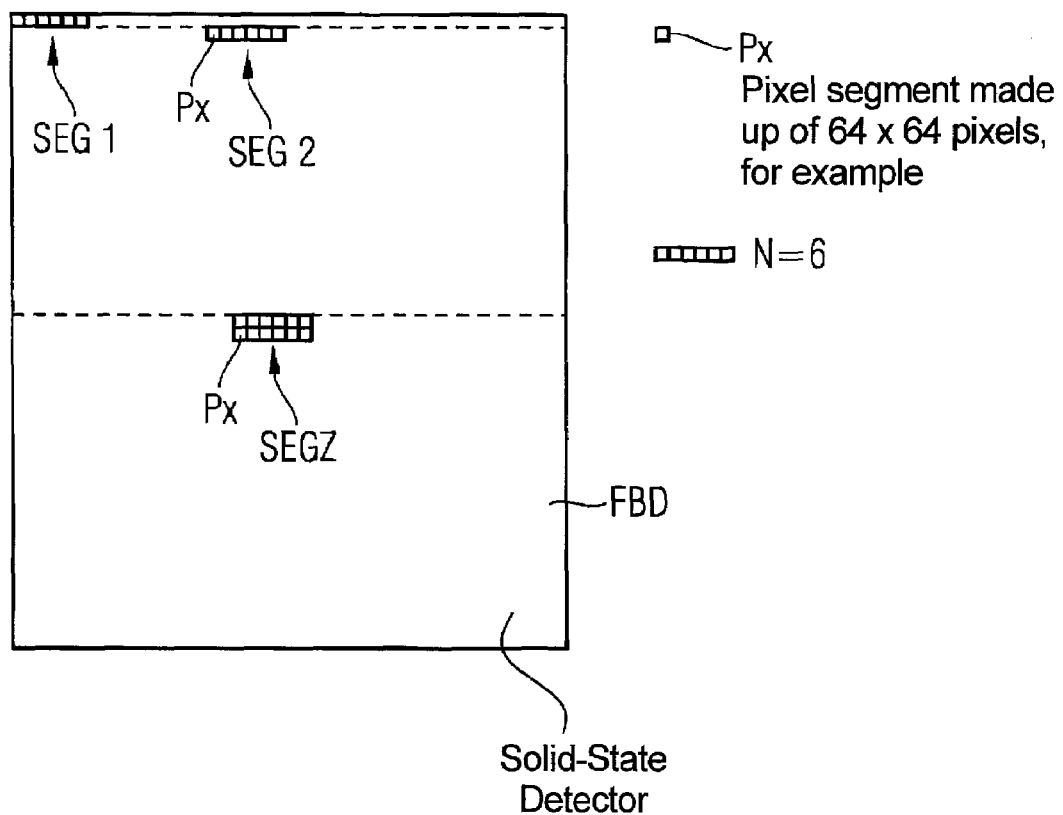
FIG. 3 shows an arrangement of image segments within a flat panel detector.

A flat panel detector FBD subdivided into image segments is reproduced in FIG. 3. The image segments SEG1 and SEG2 are thereby formed from 6 pixel segments with respectively 64×64 image points, for example. The reference segment SEGZ already addressed above and arranged approximately in the center of the flat panel detector FBD can be formed from 12 image segments with respectively 64×64 image points or 256×256 image points. Conclusions regarding the crystallization are, for example, rendered by means of the rules specified above. The indication of a defect can accordingly be conveyed with a first signaling S2, the marking of the detected regions with the second signaling S2 or a further monitoring of the flat panel detector with a third signaling S3. As indicated above, the following additional functionalities can be provided in the monitoring unit UEB: the measured values are relayed to a control unit C, BE or service center via, for example, remote service, radio or e-mail etc. The crystalline regions can be directly indicated on a screen or the flat panel detector via a direct communication to the diagnosis unit and an exchange of the flat panel detector can be indicated under consideration of requirement and quality criteria. The respective region of the crystalline detectors can additionally be marked by a service interface of the appertaining solid-state detector unit. The operator can additionally zoom out and examine more closely the appertaining region. The respective image segments with beginning or already present crystallization can be determined from the derived values and the values stored in the evaluation unit AWE from past and current measurements of signal grey values.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device for monitoring semiconductor material in a solid-state image detector comprising:
   an image acquisition unit that obtains and stores a test image produced with an image detector comprising amorphous semiconductor material;
   a monitoring unit that identifies signal values in the test image originating from respectively different regions of the test image and that compares the respective signal values to at least one threshold that characterizes a degree of crystallinity in the respective regions, said monitoring unit identifying and indicating, dependent on the comparison, any of said regions that have an unacceptable degree of crystallinity, making said regions not suitable for further use for imaging.

2. A device as claimed in claim 1 comprising a testing unit in said monitoring unit that sub-divides said image into image regions comprising pixel segments, and wherein said monitoring unit compares said pixel segments to said at least one threshold.

3. A device as claimed in claim 1 comprising a cache for storing a dark current image as said test image that is accessible by said image acquisition unit.

4. A device as claimed in claim 1 comprising a marking module in said monitoring unit that generates a visual marking of any region of said image detector that is not suitable for further use.

5. A method for monitoring semiconductor material in a solid-state image detector comprising the steps of:
   acquiring and storing a test image produced with an image detector comprising amorphous semiconductor material;
   automatically identifying signal values in the test image originating from respectively different regions of the test image and comparing the respective signal values to at least one threshold that characterizes a degree of crystallinity in the respective regions, and identifying and indicating, dependent on the comparison, any of said regions that have an unacceptable degree of crystallinity, making said regions not suitable for further use for imaging.

6. A method as claimed in claim 5 comprising sub-dividing said image into image regions comprising pixel segments, and comparing said pixel segments to said at least one threshold.

7. A method as claimed in claim 5 comprising acquiring and storing a dark current image as said test image.

8. A method as claimed in claim 5 comprising generating a visual marking of any region of said image detector that is not suitable for further use.

9. A device as claimed in claim 1 wherein said test image is comprised of pixels, and wherein said monitoring unit identifies grey signal values in said test image from each of said pixels and compares the respective grey signal values of said pixels to a reference grey value for an individual pixel, as said threshold.

10. A device as claimed in claim 1 wherein said test image is comprised of pixels, and wherein said monitoring unit identifies an average of grey signal values for a plurality of pixels in the respectively different regions, and compares said average to a standard grey signal average, as said threshold.

11. A method as claimed in claim 5 wherein said test image is comprised of pixels, and wherein the step of identifying signal values comprises identifying grey signal values in said test image from each of said pixels and wherein the step of comparing comprises comparing the respective grey signal values of said pixels to a reference grey value for an individual pixel, as said threshold.

12. A method as claimed in claim 5 wherein said test image is comprised of pixels, and wherein the step of identifying signal values comprises identifying an average of grey signal values for a plurality of pixels in the respectively different regions, and wherein the step of comparing comprises comparing said average to a standard grey signal average, as said threshold.

* * * * *